United States Patent
Gantes

(10) Patent No.: US 10,052,160 B2
(45) Date of Patent: *Aug. 21, 2018

(54) ROBOTIC SURGERY SYSTEM

(71) Applicant: Bernard Gantes, Long Beach, CA (US)

(72) Inventor: Bernard Gantes, Long Beach, CA (US)

(73) Assignee: Cyber-Implants, LLC, Huntington Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/384,073

(22) Filed: Dec. 19, 2016

(65) Prior Publication Data

US 2017/0095294 A1    Apr. 6, 2017

Related U.S. Application Data

(63) Continuation of application No. 13/215,985, filed on Aug. 23, 2011, now Pat. No. 9,522,046, and a continuation of application No. 12/245,697, filed on Oct. 3, 2008.

(Continued)

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *A61B 34/30* (2016.02); *A61C 1/084* (2013.01);
(Continued)

(58) Field of Classification Search
CPC ..... A61B 17/15; A61B 19/22; A61B 19/2203; A61B 19/50; A61B 19/52; A61B 19/5212;
(Continued)

(56) References Cited

U.S. PATENT DOCUMENTS

| 5,086,401 A | * | 2/1992 | Glassman | A61B 34/20 606/53 |
| 5,279,309 A | * | 1/1994 | Taylor | A61B 34/20 600/595 |

(Continued)

*Primary Examiner* — Crystal J Barnes-Bullock
(74) *Attorney, Agent, or Firm* — Rutan & Tucker LLP; Hani Z. Sayed

(57) ABSTRACT

A surgical apparatus, system and methodology are provided that may be utilized to treat a plurality of medical conditions. A robotic apparatus may be utilized in the treatment of a medical condition or to assist a medical professional in a surgical procedure. Additionally, the robotic apparatus and system may be utilized during a surgical procedure to provide guidance and to narrow the margin of error. In an exemplary embodiment, a scan may first be performed on a patient to determine a plurality of surgically necessary characteristics, such as bone density, locations, and the like. A virtual treatment plan may be provided by the system. An active and/or passive robotic apparatus may be provided to assist in the surgical technique. The robotic apparatus may be an active robotic which includes surgical tools whereby the medical professional may perform the surgical technique with the assistance of the active robotic apparatus.

20 Claims, 11 Drawing Sheets

Related U.S. Application Data

(60) Provisional application No. 61/376,129, filed on Aug. 23, 2010, provisional application No. 60/977,368, filed on Oct. 3, 2007.

(51) Int. Cl.
| | |
|---|---|
| *A61B 34/30* | (2016.01) |
| *A61C 1/08* | (2006.01) |
| *A61C 9/00* | (2006.01) |
| *A61C 13/00* | (2006.01) |
| *A61B 90/00* | (2016.01) |

(52) U.S. Cl.
CPC ............ *A61C 9/004* (2013.01); *A61C 9/0086* (2013.01); *A61C 13/0004* (2013.01); *A61B 2034/102* (2016.02); *A61B 2034/105* (2016.02); *A61B 2034/108* (2016.02); *A61B 2090/3735* (2016.02); *G06T 2210/41* (2013.01); *Y10S 128/92* (2013.01); *Y10S 128/922* (2013.01)

(58) Field of Classification Search
CPC ............ A61B 19/56; A61B 2019/2292; A61B 2019/501; A61B 2019/502; A61B 2019/505; A61B 2019/507; A61B 2019/508; A61B 2019/562; A61B 34/10; A61B 34/20; A61B 34/25; A61B 34/30; A61B 2034/105; A61B 2034/108; A61C 1/084; A61C 8/00; A61C 8/009; A61C 9/004; A61C 13/0004; A61C 13/08; A61C 19/04; G06F 17/5009; G06F 19/3437; Y10S 128/92; Y10S 128/922; G06T 2210/41

See application file for complete search history.

(56) References Cited

U.S. PATENT DOCUMENTS

| | | | | |
|---|---|---|---|---|
| 5,320,529 A | * | 6/1994 | Pompa | A61C 1/084 433/214 |
| 5,769,092 A | * | 6/1998 | Williamson, Jr. | A61B 17/8847 128/898 |
| 5,806,518 A | * | 9/1998 | Mittelstadt | A61F 2/30942 128/920 |
| 5,871,018 A | * | 2/1999 | Delp | A61B 17/154 128/898 |
| 5,951,475 A | * | 9/1999 | Gueziec | G06T 3/0068 128/922 |
| 6,224,373 B1 | * | 5/2001 | Lee | A61B 6/14 433/172 |
| 6,711,432 B1 | * | 3/2004 | Krause | A61B 17/15 128/922 |
| 8,046,054 B2 | * | 10/2011 | Kim | A61B 6/4014 378/4 |
| 8,147,503 B2 | * | 4/2012 | Zhao | G06K 9/3241 382/128 |
| 8,311,791 B1 | * | 11/2012 | Avisar | G09B 23/28 702/19 |
| 8,398,541 B2 | * | 3/2013 | DiMaio | A61B 19/2203 348/211.3 |
| 8,753,346 B2 | * | 6/2014 | Suarez | A61B 17/162 606/81 |
| 8,801,719 B2 | * | 8/2014 | Park | A61B 17/154 606/86 R |
| 2006/0106369 A1 | * | 5/2006 | Desai | A61B 34/70 606/1 |
| 2006/0127848 A1 | * | 6/2006 | Sogo | A61C 1/084 433/173 |
| 2009/0092948 A1 | * | 4/2009 | Gantes | A61C 1/084 433/215 |
| 2010/0255445 A1 | * | 10/2010 | Gantes | A61C 1/084 433/173 |
| 2010/0317965 A1 | * | 12/2010 | Itkowitz | A61B 34/37 600/425 |
| 2011/0130761 A1 | * | 6/2011 | Plaskos | A61B 17/155 606/87 |
| 2011/0245951 A1 | * | 10/2011 | Gantes | A61C 1/084 700/98 |
| 2011/0256508 A1 | * | 10/2011 | Gantes | A61C 1/084 433/215 |
| 2016/0278870 A1 | * | 9/2016 | Quaid | A61N 1/372 |

\* cited by examiner

ROBOTIC SURGERY SYSTEM

PRIORITY CLAIM

This application is a continuation of U.S. Utility application Ser. No. 13/215,985, filed on Aug. 23, 2011, entitled "Robotic Surgery System", now U.S. Pat. No. 9,522,046, which claims priority to the earlier filed U.S. Provisional Application No. 61/376,129, filed on Aug. 23, 2010 and a continuation of U.S. Utility application Ser. No. 12/245,697, filed on Oct. 3, 2008, entitled "Assisted Dental Implant Treatment" which claims priority to U.S. Provisional Application No. 60/977,368 filed on Oct. 3, 2007. Each of these applications are incorporated by reference.

FIELD OF THE INVENTION

The field of the invention is for a robotic assisted surgery. More specifically, the field of invention is for the use of a robotically assisted system which allows for guidance of an apparatus by a medical professional during a surgical and/or medical procedure.

BACKGROUND

Many minimally invasive medical techniques are aimed at reducing the amount of damage done to tissue during the exploratory diagnostic or surgical procedures. The net effect of these less invasive techniques is to reduce patient recovery time, discomfort, and adverse side effects. Among the many medical procedures performed each year, many can potentially be performed in a minimally invasive manner. However, only a relatively small number of surgeries currently use these techniques due to limitations in minimally invasive surgical instruments and techniques as well as the additional surgical training required to master them.

Advances in minimally invasive surgical technology could dramatically increase the number of surgeries performed in a minimally invasive manner. The average length of a hospital stay or the number of medical visits are typically greater in traditional prior art surgical techniques than for minimally invasive surgical techniques. Thus, the complete adoption of minimally invasive techniques could produce significant savings in hospital and/or dental visits and patient recovery, such as discomfort, side effects and reduced down time for the individual patient.

There are many types of minimally invasive medical techniques including endoscopy, laparoscopy, certain cosmetic surgery techniques and the like. Generally, the type of instruments needed in these medical procedures, include clamps, graspers, scissors, staplers or needle holders. The working tools or instruments are similar to those used in a conventional (open) surgery but with the addition of an extension portion. In performing the medical procedure, a medical professional passes the working tools or instruments into the patient and will manipulate them from outside the patient with the assistance of a television monitor or the like.

Additionally, many medical procedures may allow for the medical professional to oversee the procedure by utilizing a monitor, whereby a camera is mounted to the medical device utilized in the procedure.

However, there are a variety of disadvantages relating to minimally invasive surgical techniques. For example, existing minimal invasive techniques still require the utilization of instruments that deny the surgeon flexibility of tool placement found in an open surgery. Most current minimally invasive tools have rigid shafts and the difficulty experienced in approaching the medical procedure site. Additionally, the length and construction of many instruments reduces the medical professional's ability to feel forces exerted by tissues and organs on the end effector of the associated tool. The lack of dexterity and sensitivity of these tools is a major impediment to the expansion of minimally invasive procedures.

Additionally, another disadvantage is that the medical procedure is still performed by a medical profession that may be prone to mistakes, slips and the like. Human error is always an issue in any medical procedure.

With advances in computer technology, it is now possible for computer controlled robotic systems to accept, interpret data and control a robotic system during a medical procedure. Unfortunately, robotic arms often have responsive limitations which may be more restrictive than a human medical professional. Furthermore, the robotic arm joints often have limits in their displacement capability or range of achievable position relative to each other. Further, the robotic arm and surgical instrument assemblies may have positional limits beyond which it is not possible to move.

Another problem with active computer controlled robotic system is that they require significant operational costs in the form of structural elements necessary to run the robotic system, including motors, significant power supply to power the motors, electrical connections, active actuators and computer systems to link the robot to the computer controlling programs.

Moreover, sufficient data must be inputted into the robotic system such that the robot knows the type of procedures and restrictions required during the medical procedure. The robotic systems are typically not adaptable. Therefore, if a patient moves prior to the procedure, the robotic system may be misaligned to the proper points of procedure and significant mistakes may be made. Typically, a medical procedure must be supervised by a medical professional in order to insure proper technique and application to the individual patient. Constant supervision by the medical professional and adaption is necessary must be contemplated.

The object of this invention is to provide a method and control system whereby a robotic surgery/medical procedure technique may be sufficiently controlled by the system and whereby treatment and planning systems are all done by the system. Currently, a need exists for a passive robotic system which allows for control of a passive actuator without the need for cost prohibitive robotic motors and the like.

Therefore, a need exists for a surgical/medical procedure that may be performed by a passive robotic system after collection of information from the patient scans and after sufficient analysis and models have been made by the system. Further exists for a medical procedure to be performed by a passive robotic system whereby the system may be guided simply by a medical professional after a treatment plan has been effectuated and the system utilizes the scanned data and the treatment plan to properly perform the surgical and/or medical procedure, once those plans have been detailed and accepted by a medical professional.

SUMMARY OF THE INVENTION

A surgical apparatus, system and methodology is provided. The surgical method and system may be utilized to treat a plurality of medical conditions and/or utilized in surgical settings. The system enables a robotic apparatus in the treatment of a medical condition or to assist a medical professional while performing a surgical procedure, to provide guidance thereby narrowing the margin of error. In an exemplary embodiment, a scan, preferably a CT scan, may first be performed on a patient to determine a plurality of surgically information, including, but not limited to bone density, locations, and the like. After the scan has been performed, a virtual treatment plan may be provided by the system and an active and/or passive robotic apparatus may be provided to a medical professional, which may assist in the surgical procedure. The robotic apparatus may be an active robotic apparatus which includes the surgical tools utilized by a medical professional whereby the medical professional may at least partially perform the surgical technique with the assistance of the active robotic apparatus. In an exemplary embodiment, a passive robotic apparatus may be provided without the active robotic components, such that the medical professional may simply guide the apparatus during the medical and/or surgical procedure whereby the robotic apparatus may be programmed to provide feedback and/or limitations to the medical professional's surgical movements.

To this end in an exemplary embodiment, a robotic surgical apparatus, system and method is provided whereby the system may utilize a robotic apparatus which may assist a medical professional in performing a surgical procedure.

An exemplary embodiment of the present invention, for planning and performing a surgical procedure, the system comprising: a processing portion for processing the hard tissue of a patient that communicates hard tissue data to the system; hard tissue data is communicated to the system in the form of a three-dimensional (3-D) representation of the hard tissue; a fabrication module that based on the 3-D representation data, produces a physical model of the hard tissue; a treatment planning portion for desired treatment of the patient; and a surgical robot apparatus to allow for health care professional to utilize same in a surgical procedure.

In an exemplary embodiment, wherein the surgical procedure is a surgical technique on a patient's hard tissue.

In an exemplary embodiment, further comprising a surgical module that based on the 3-D representation data, guides the medical professional in the surgical procedure.

In an exemplary embodiment, wherein the robotic apparatus is an active robotic whereby the robotic apparatus is controlled by a computer program.

In an exemplary embodiment, wherein the robotic apparatus is a passive robotic whereby the robotic apparatus is controlled by a medical professional with limited feedback from the robotic apparatus.

In an exemplary embodiment, wherein the treatment planning portion includes combining the 3-D representation data and input received from a treatment planner and outputs a treatment plan for implementation of the treatment plan by the surgical robot.

In an exemplary embodiment, wherein the system may utilize a software to digitally fabricate a computerized image of the patient's hard tissue to illustrate the treatment plan for the individual patient.

In an exemplary embodiment, further comprising: a surgical guide based on the digitally fabricated computerized image which is utilized by the robotic surgical tool.

An exemplary embodiment of the present invention, a method for planning and performing a surgical procedure, the method comprising: providing a system for planning and performing a surgical procedure including: providing a processing portion for processing hard tissue information about a patient; communicating hard tissue information in the form of a three-dimensional (3-D) representation; providing a physical model of the patient's mouth using a fabrication module; providing a surgical robot apparatus utilizable by a health care professional; and utilizing the surgical robot apparatus to perform the surgical procedure.

In an exemplary embodiment, wherein the surgical procedure is a surgical technique on a patient's hard tissue.

In an exemplary embodiment, wherein the surgical robot apparatus module guides the medical professional in the surgical procedure.

In an exemplary embodiment, wherein the robotic apparatus is an active robotic whereby the robotic apparatus is controlled by a computer program.

In an exemplary embodiment, wherein the robotic apparatus is a passive robotic whereby the robotic apparatus is controlled by a medical professional with limited feedback from the robotic apparatus.

In an exemplary embodiment, wherein a treatment planning portion includes combining the 3-D representation data and input received from a treatment planner and outputs a treatment plan for implementation of the treatment plan by the surgical robot.

In an exemplary embodiment, further comprising the step of: utilizing software to digitally fabricate a computerized image of the patient's hard tissue to illustrate the treatment plan for the individual patient.

In an exemplary embodiment, further comprising the steps of: digitally fabricating a computerized image which is utilized by the surgical robotic apparatus.

In an exemplary embodiment, a method for planning and performing a surgical procedure, the method comprising the steps of: processing hard tissue of a patient; communicating hard tissue data to a surgical procedure system in the form of a three-dimensional (3-D) representation of the hard tissue; producing a physical model of the hard tissue; and utilizing a surgical robot apparatus in a surgical procedure.

In an exemplary embodiment, wherein the surgical robot apparatus is guided by a medical professional in the surgical procedure.

In an exemplary embodiment, wherein the robotic apparatus is controlled by a computer program.

In an exemplary embodiment, wherein the robotic apparatus is controlled by a medical professional with limited feedback from the robotic apparatus.

In an exemplary embodiment, a robotic surgical apparatus and system is provided whereby the surgical apparatus may improve patient recovery time, as well as surgical efficiency.

Still another exemplary embodiment is to provide a robotic surgical apparatus and system whereby the robotic surgical apparatus may decrease errors made by the medical professional during a surgical procedure.

In another exemplary embodiment, a robotic surgical apparatus and system is provided whereby the apparatus may utilize a plurality of actuators through which the passive actuators may allow for the robotic apparatus to be operated without the need for motors, gears and significant electrical wiring.

Still another exemplary embodiment is to provide a robotic surgical apparatus and system whereby the robotic apparatus may utilize motors, gears, wiring and proprietary software to guide a medical professional in a surgical technique.

In an exemplary embodiment, a robotic surgical apparatus, system and method is provided to assist a medical professional in the process of a medical procedure involving hard tissues of the human body.

In an exemplary embodiment, a robotic surgical apparatus and system may be provided whereby the robotic surgical apparatus may allow for more precise surgical techniques to be performed by a medical professional.

In an exemplary embodiment, a robotic surgical apparatus and system may be provided whereby the planning and medical procedure is contemplated by which the system first allows for a CT scan to be made of the bone structure of a patient prior to surgical procedure.

In an exemplary embodiment, a robotic apparatus and system may be provided whereby the system may utilize information from the bone imaging scan to create a 3-D representation of the patient's bone structure to enable more precise surgical techniques.

In yet another exemplary embodiment, a robotic surgical apparatus and system may be provided whereby the system may also provide a treatment planning process which combines a scan of the bone of each individual patient with a 3-D model information of the patient's bone scan to determine a plurality of characteristics including at least one of a spatial location, a depth, a diameter, and an angular orientation of a surgical technique to follow by the robotic apparatus.

Still another exemplary embodiment is to provide a robotic surgical apparatus and system whereby the system may allow a medical professional to direct a surgical robot to perform a surgical technique on the hard tissue of a patient based on a treatment plan.

Another exemplary embodiment is to provide a robotic surgical apparatus and system whereby the robotic surgical apparatus may be programmed with scanned images of a patient's hard tissues such that the robotic surgical apparatus will eliminate or greatly reduce any errors by the medical professional during the surgical procedure.

Yet another exemplary embodiment is to provide a robotic surgical apparatus and system whereby a medical professional may be able to direct a surgical robot to perform a surgical technique on a patient's hard tissue based on the treatment plan from a CT scan of the patient's hard tissues.

Another exemplary embodiment of the present invention is to provide a robotic surgical apparatus and system by which the system allows for a medical professional to direct a surgical robot to perform a surgical procedure on the hard tissue of a patient, whereby the robotic apparatus is passive and thereby allows direction by the medical professional.

In yet another exemplary embodiment, a robotic surgical system and method is provided whereby the health professional may guide the surgical robot and the robotic apparatus, providing feedback to determine the limits of the surgical technique on the patient, thereby greatly reducing accidents and surgical errors during the procedure.

In another exemplary embodiment, a robotic surgical apparatus and system is provided whereby the system may include at least a guidable passive robotic apparatus having at least an actuator, such that an instrument connected to the passive robotic apparatus may only perform one or more given movements, due to the control signals influencing at least one passive actuator, under the influence of an external force from a health care professional performing the surgical technique.

In an exemplary embodiment, a passive robotic apparatus and system is provided whereby the apparatus may have an actuator that may be guided to a particular place which is desired by the health care professional. The system may utilize an actuator which may have specific metes and bounds determined by the surgical technique and pre-determined axis configurations that allow movement of the passive actuator to only a small divergence from the set points taken from a mapping/scan previously taken of the individual patient's hard tissue.

Furthermore, it is possible to define for example a radius of action for the medical instrument, in which it can be moved, wherein at least one controllable passive actuator can increasingly impede or brake movement of the instrument towards an area which is inaccessible for the instrument and for example creates a complete blockage at the border of the area.

Among the many different possibilities contemplated, a robotic surgical apparatus and system may be provided whereby the system further comprises the program which controls movement of the surgical robot apparatus such that the robotic apparatus is only capable of moving based on pre-determine guidelines and whereby the ultimate control of the robotic system is by a health care professional but the programming limits errors by the medical and/or health care professional.

In an exemplary embodiment, a robotic surgical apparatus and system is provided whereby the system further includes a treatment planner which incorporates information from a CT scan of a patient's hard tissue, then plans for treatment by utilizing a computer program and allowing the surgical robotic apparatus to be utilized to effectuate the surgical procedure based on the treatment planner.

In still another exemplary embodiment, a robotic surgical apparatus and system is provided whereby the system has a treatment planning process that combines 3-D images from a patient's CT scan with inputs received from a treatment planner and then outputs a treatment plan having at least one of a spatial location, depth, diameter, and an angular orientation of a surgical technique to be performed by a medical professional.

In yet another exemplary embodiment, a robotic surgical apparatus and system provided whereby the system may utilize images of a patient's hard tissue structures from a computed tomography, x-ray, magnetic resonance imaging, optical imaging, acoustic imaging, and optical coherence tomography.

In still another exemplary embodiment, a robotic surgical apparatus and system is provided whereby the system may utilize surface data derived from imaging of hard tissues from a patient. In some embodiments, the imaging of the hard tissues comprises imaging with at least one of computed tomography, x-ray, magnetic resonance imaging, optical imaging, acoustic imaging, and optical coherence tomography.

Yet another exemplary embodiment is to provide a robotic surgical apparatus and system whereby bone data may be inputted into the system and the bone data may be derived from imaging by at least one of computed tomography, x-ray, and magnetic resonance imaging. In some embodiments, one imaging device comprises both the bone imaging information and the surface imaging information.

Still another exemplary embodiment is to provide a robotic surgical apparatus and system whereby the system provides a surgical system having a robot that, based on the treatment plan, may guide the medical professional through a surgical technique.

Another exemplary embodiment is to provide a robotic surgical apparatus and system whereby the system coordinates treatment planning, scans of the hard tissue from the patient, and the surgery procedure with the use of computer software which guides the medical professional through the surgical procedure.

DETAILED DESCRIPTION OF THE PREFERRED EMBODIMENT

The systems and methods described herein generally relate to robotic assisted surgery which allow for guidance of an apparatus by a medical professional during a surgical and/or medical procedure. One example system presented herein can be used for the design and delivery of dental prostheses. It will be understood by those of skilled in the art, that these systems and methods may be applied to a variety of surgeries that might be robotic assisted.

Conceptually, there are several phases involved in the design and delivery of dental prostheses. Generally speaking, the overall process can be broken into several interdependent phases that include, without limitation, evaluation of the patient, treatment planning, manufacture of the prosthesis, surgical procedures to prepare the patient's oral structures to receive the prosthesis, and finally, delivery of the prosthesis. In various embodiments of the systems and methods described herein surgical procedures to prepare the patient's oral structures to receive the prosthesis, delivery of the prosthesis, or both might be performed using systems or apparatuses for robotic assisted surgery.

Figure 1:
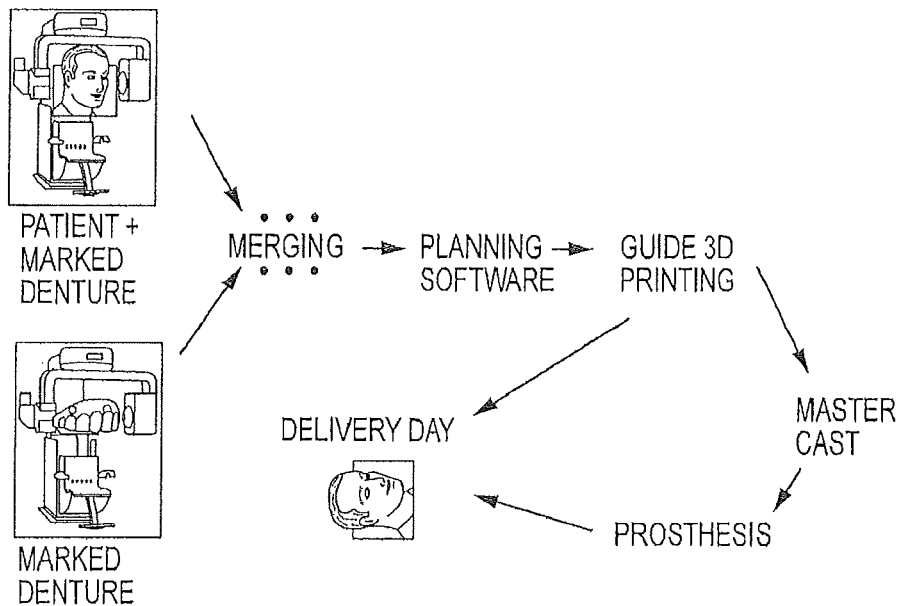
FIG. 1 is a flowchart depicting a prior art system for planning and delivering dental implants.
Figure 2:
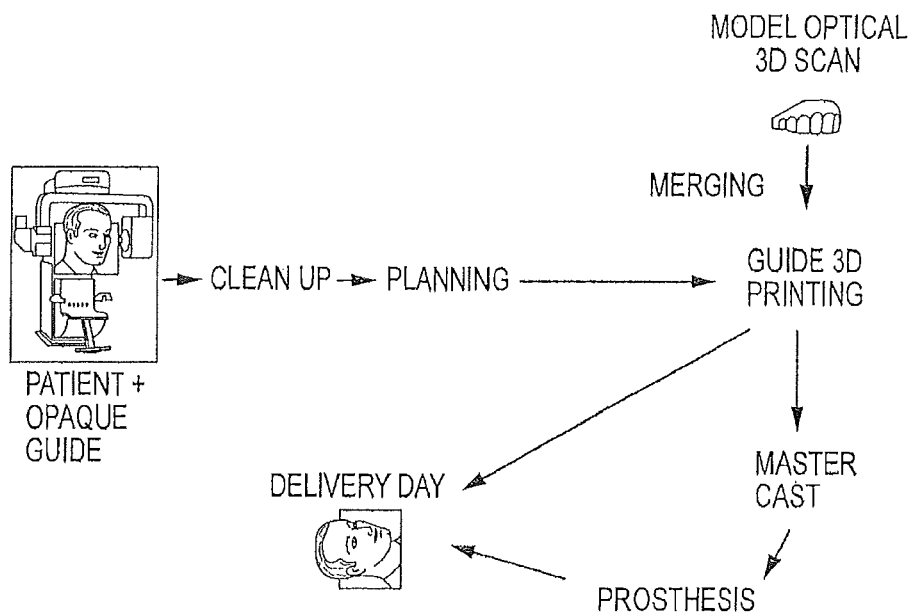
FIG. 2 is a flowchart depicting another prior art system for planning and delivering dental implants.

In certain prior art systems, such as the systems in FIG. 1 and FIG. 2, part of the initial evaluation of the patient involves CT scanning to determine the location and quality of the underlying bony components of the patient's jaw around the intended surgical site. For example, in the NobelGuide™ system, CT imagery of the patient's oral structures, and a marked denture, are merged using computer software to produce a "virtual" representation of the patient's surface oral features, in relation to the underlying hard tissue such as bone and existing teeth. If desired, existing prosthetics can be included in the CT scan as long as they are made of materials that do not generate significant scatter artifact.

This virtual representation is then imported into treatment planning software. Here, a dental professional plans the placement of osteotomy holes in the patient's gum and jaws that will receive dental implant posts. The dental prosthesis is ultimately mounted on these implant posts. The procedure can involve the placement of a single hole adapted to receive a single implant where an individual tooth is to be replaced, or multiple holes where multiple prosthetic teeth, or a row of prosthetic teeth are to be installed.

In the prior art systems, the virtual treatment plan is generally exported to an offsite facility where a surgical guide is manufactured by sterolithography. Depending on the complexity of the object to be made, sterolithography can take anywhere from a few hours to more than a day to complete. Once completed, the surgical guide is packaged and returned to the dental professional.

The surgical guide is used as a template both for the making of a master cast from which the prosthesis is derived, as well as for performing the surgical procedure. The guide includes drill guides, typically metal bushings that define the angle and depth to which an osteotomy hole will be drilled in the patient's jaw during the surgical step.

In performing the surgery, the dental professional places the guide on the patient's gum, attempts to confirm proper registration of the guide with the gum structure, and then anchors the guide in place by drilling into the jaw and then anchoring the guide with mounting screws. As the surgical guide provides the treatment plan, key to the success of the procedure is the fit of the surgical guide. Unfortunately, due a number of factors, fit can sometimes be a problem. These include problems with the CT data related to artifacts, or lack of fidelity due to data optimization between scan layers, poor fit between the soft tissues of the patient and the hard master cast, etc.

In addition, since the surgery can take place at a significant time after the original CT scan and other measurements were taken to provide the data to produce the guide, there is always a risk that on the day of surgery the guide will not fit well, due to changes in the soft tissue overlying the jaw bones. In addition, since sterolithography resin materials are generally sensitive to moisture, changes in the shape of the guide itself can occur, reducing the fidelity of fit to the patient.

Figure 3:
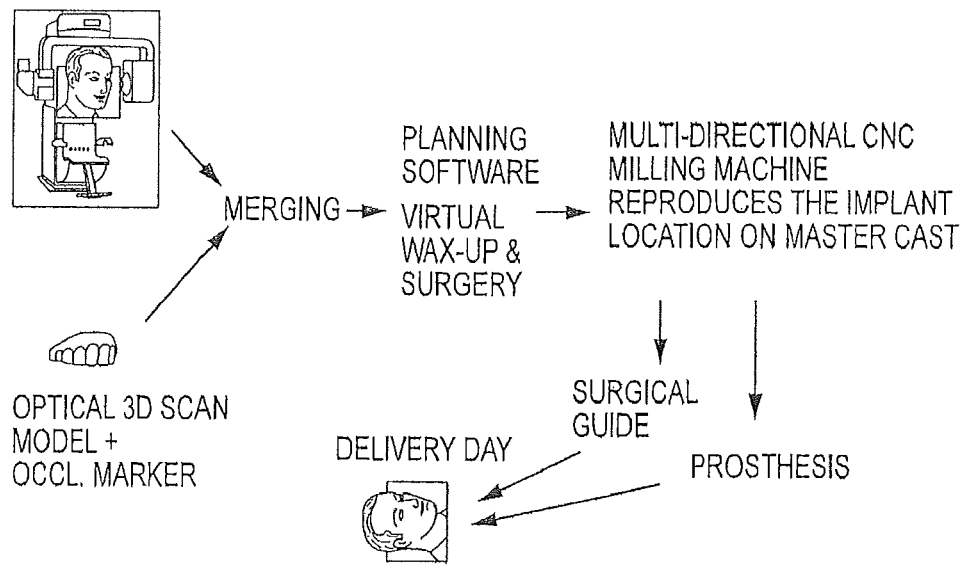
FIG. 3 is a flowchart of steps of an embodiment of a method of planning and delivering a dental prosthesis to a patient using a surgical guide produced by a multi-axis milling machine, according to the present disclosure.
Figure 4:
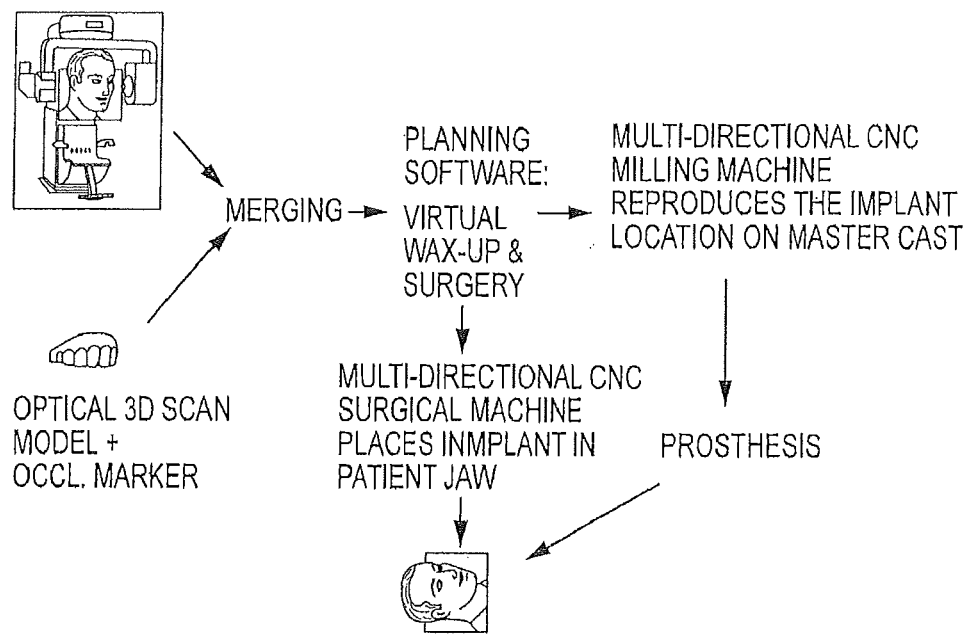
FIG. 4 is a flowchart of steps of an embodiment of a method of planning and delivering a dental prosthesis to a patient using a surgical robot, according to the present disclosure.

Therefore, embodiments of the present disclosure are directed towards a system and apparatus for use in planning treatment, performing surgery, manufacturing a dental prosthesis, and delivering the prosthesis to a patient, with high fidelity, and in a minimum time period. In particular, the described embodiments are adaptable to a system where a patient is scanned, the treatment parameters determined, and the surgery performed within a single day. FIGS. 3 and 4, provide flowchart examples of processes of planning and delivering dental implants and prostheses that improve upon the prior art. It will be understood that any of the disclosed embodiments are merely exemplary, and as such do not limit the scope of the disclosure.

Patient Imaging

As with prior art dental implant treatment systems, in the system of the present disclosure, information regarding surface and bone structures of the patient's oral and facial regions are important in implantation planning, execution of the implantation plan, and the manufacture and delivery of the finished endosseous implants and prosthesis.

Figure 5:
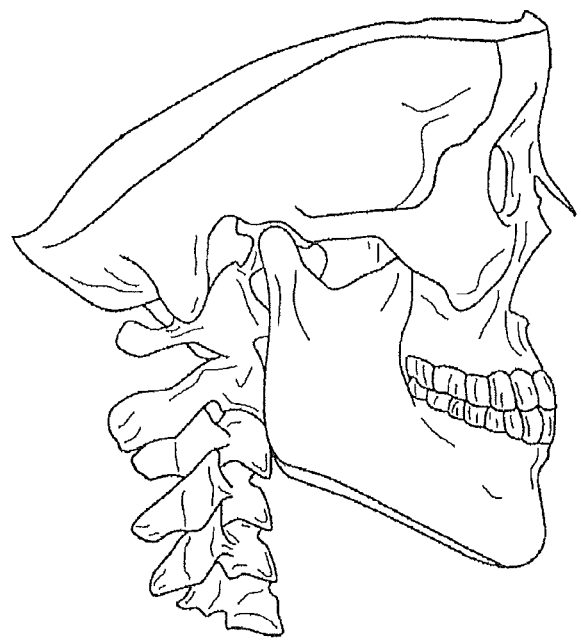
FIG. 5 is an example of a three-dimensional reconstruction of a patient's oral structures derived from computed tomography (CT) scan data.

In certain embodiments, bone structures are imaged by a bone imaging module. In some embodiments, the bone imaging module includes a CT system. In certain embodiments, imaging can be of the patient's mandible, maxilla, or both, and can include the entire bony structure of the jaw or a portion thereof. In certain embodiments, imaging can include additional bones of the skull of the patient outside the oral regions proper. An example of a CT image is provided in FIG. 5.

Various CT modalities are available that are useful in conjunction with the present system. For example, in some cases traditional spiral CT can be used. In some cases, it can be desirable to use other imaging modalities, for example and without limitation, cone beam CT. The precise type of imaging is not necessarily limiting to the embodiments of the present disclosure.

In certain embodiments, surface imaging can be achieved by optical coherence tomography ("OCT") techniques. In certain OCT techniques, an optical fiber splitter splits light from a broad band light source into optical fibers, one of the optical fibers directing light to a sample (e.g., an oral surface and a facial surface) path and another of the optical fibers directing light to a reference path mirror. A distal end of the sample path fiber can interface with a scanning device, or the like, and light reflected from the scanning device can be recombined with the signal from the reference mirror to form interference fringes that provide for precise depth-resolved imaging or optical measurements. Certain OCT techniques can measure spatially resolved backscattered intensity with a resolution on the order of a few micrometers.

Certain OCT techniques, such as Fourier domain OCT ("FD-OCT"), can achieve a high sensitivity image and a rapid imaging speed. Certain OCT techniques, such as polarization sensitive Fourier domain OCT ("PS-FD-OCT"), can reveal birefringence, diattenuation, and polarization sampling by measuring a change in polarization state. The implementation of polarization sensitivity into FD-OCT as known in the art. Certain FD-OCT systems which implement polarization sensitivity can comprise dual-channel detection paths, with two separate spectrometers, two separate line-scan cameras, or two separate lines on an area-scan camera to capture, in parallel, the spectral interferogram for two orthogonal polarization modes. Certain swept source implementations of PS-FD-OCT can employ two detection channels in a configuration similar to time-domain polarization sensitive OCT.

Certain OCT techniques can involve, e.g., a light source comprising a Ti:Al2O3 mode-locked femtosecond laser operating at, e.g., a 88-MHz pulse repetition rate, a center wavelength $\lambda o=830$ nm, and spectral bandwidth $\Delta\lambda=55$ nm Full Width Half Maximum ("FWHM"). Light that exits the source path can be collimated in open air and injected into an interferometer with an achromatic microscope objective, giving a Gaussian beam profile with a FWHM diameter of 2 mm. In certain OCT techniques, a spectrometer can be used to monitor source spectral quality, the spectrometer detects the incident spectrum as sampled. In certain OCT techniques, viewing of the incident beam location on the tissue specimen can be achieved with, e.g., visible red light ($\lambda o=660$ nm), emitted by, e.g. a diode laser coupled into a multimode fiber, collimated, and combined with the source beam by a dichroic mirror. A Glan-Thompson prism polarizer can be oriented at 45° to ensure that light injected into the interferometer has equal amplitudes and zero relative phase in horizontal and vertical polarization channels. The angular orientation of all PS-OCT polarization elements can be measured clockwise with respect to the horizontal plane (x axis) viewed along the beam propagation direction (z axis); the y-axis is parallel to the Earth's gravitational field. Certain OCT techniques can be performed with continuous-wave light without the need for ultrashort laser pulses. For instance, in low-coherence reflectometry, the coherence property of light returning from an imaged sample provides information on the time-of-flight delay from reflective boundaries and backscattering sites in the sample. Optical coherence tomography's resolution is limited only by the coherence length of the optical source. Certain OCT techniques can be performed with a fiber optic Michelson interferometer illuminated by low-coherence light from, e.g., a super luminescent diode (SLD) which operates at a wavelength of 830 nm and at an optical power of 20 µW.

In certain embodiments, the light source can be a high speed scanning laser HSL-2000 with an instantaneous coherence length of over 10 mm. The swept laser source includes emitted light with a mean frequency of the output spectrum that varies over time. The mean frequency of light emitted from the swept source may change continuously over time at a tuning speed that is, e.g., greater than 100 terahertz per millisecond and repeatedly with a repetition period. A swept laser source may be any tunable laser source that rapidly tunes a narrowband source through a broad optical bandwidth. The tuning range of a swept source may have a tuning range with a center wavelength between, e.g., approximately 500 nanometers and 2000 nm, a tuning width of approximately greater than 1% of the center wavelength, and an instantaneous line width of less than approximately 10% of the tuning range. In certain embodiments, a swept laser source is coupled to an electro-optic polarization modulator to modulate the polarization state of the source light periodically in time between two semi-orthogonal polarization states.

In certain embodiments, surface imaging can be achieved by optical imaging, such as with a camera. In certain embodiments, the camera can record images on film. In certain embodiments, the camera can record images in digital format. In certain embodiments, a camera can be configured to record images with visible light, UV light, blue light, red light, infrared light, or combinations thereof. In certain embodiments, surface imaging can be achieved by acoustic imaging, such as ultrasound imaging.

In certain embodiments, surface imaging can be achieved by photoacoustic imaging, in which non-ionizing laser pulses are delivered to imaged surfaces. In certain embodiments, surface imaging can be achieved by thermoacoustic imaging in which radio frequency pulses are delivered to imaged surfaces. In certain embodiments of photoacoustic and thermoacoustic imaging, some of the delivered energy is absorbed by the imaged service and converted into heat, which means to transient thermoelastic expansion and a wideband (e.g., MHz) ultrasonic emission. The generated ultrasonic waves can be detected by ultrasonic transducers and processed to form images. In certain embodiments of photoacoustic imaging and thermoacoustic imaging, the magnitude of the ultrasonic emission, which is proportional to the local energy deposition, reveals physiologically specific optical absorption contrast from which 2-D or 3-D images of the targeted areas can then be formed.

In certain embodiments, surface imaging, bone imaging, or combinations thereof can be achieved by CT, magnetic resonance (MR) imaging, x-ray imaging, or combination thereof.

In certain embodiments, the imaging devices can be configured to mount on an endoscope. In certain embodiments, the camera can be configured to be held by a human hand. In certain embodiments, the camera can be configured to mount on a stabilizing apparatus, such as a tripod.

In certain embodiments, service and bone imaging can include a step in which all pre-existing, removable metal-containing prostheses are removed from the imaged facial and/or all region of the patient prior to imaging in order to reduce the likelihood of scatter artifact. Where the patient has a small edentulism with stable natural occlusion, the scan can be performed without a removable scanning prosthesis, as the existing teeth are adequate to place the mandible and maxilla in a position representative of the patient's normal occlusion.

Where the patient has a large or complete edentulism, the scan can be performed with an all-acrylic functional removable prosthesis or with a functional acrylic replica. A functional prosthesis is defined as one where the prosthesis incorporates an accurate reproduction of the edentulous ridge mucosa (or gum), and an accurate and esthetically acceptable occlusal relation with the other arch. Thus, the acrylic replica simulates the space occupied by a normal set of teeth, and places the mandible and maxilla in a relatively normal position for the purposes of the scan. Those of skill in the art will readily appreciate the various functional replicas will be useful in practicing the methods of the present disclosure.

Prior to scanning with a functional replica, several x-ray labels (e.g., Surmark™ labels) can be evenly placed on the functional replica portion contacting the mucosal ridge crest. The patient can then be scanned with the replica in place. During scanning the patient is instructed to apply moderate biting force on the replica so that the oral structures remain relatively compressed. Where the patient has an unstable bite, a silicone bite block can be used during scanning to aid in maintaining a stable configuration of the oral structures.

In addition to imaging the underlying bony structures, the surface contours of at least a portion, and sometimes all, of the patient's oral structures are obtained by way of a surface imaging module. There are various methods of acquiring surface contour information, and various types of surface imaging modules that are useful in the context of the present disclosure.

In some embodiments, the surface contours of at least a portion of the patient's oral structures can be performed. Various ways of accomplishing this are possible, one of which is disclosed in U.S. Pat. No. 5,343,391 (Mushabac), by laser optical surface scans (Soncul et al., J. Oral Maxillofac. Surg., 2004, 62: 1331-1140), or using a stereo multi-camera 3-D photographic system. In some embodiments, Optical Coherence Tomography (OCT) can be used to image oral structures (Otis et al., J. Am. Dent. Assoc., 131: 511-514). The contents of each of these references are incorporated by reference in their entireties.

In some embodiments, the dental professional will make a casting of the patient's oral structures, and imaging of the cast can be performed to acquire information related to the patient's oral surface contours.

Regardless of the method employed, the result will be the acquisition of information related to the three-dimensional (3-D) relationship of the patient's existing teeth (if any) and gingiva. In some embodiments, the casting can include an occlusion marker to provide information regarding the relative meshing of the patient's upper and lower dentition.

Treatment Planning

Once data representing the surface contours of the patient's oral structures, as well as the underlying bony structures have been obtained, a computer software algorithm is used to merge the two datasets. The merged dataset provides a 3-D representation of both the surface and underlying structures. The merged data can then be used to provide a virtual 3-D representation of the patient's bony structures (derived from CT scanning) and surface features (from optical or other scanning methods)—i.e., a 3-D virtual patient reconstruction. The 3-D representation can conveniently be displayed on a computer screen or other visual display, and displays the gingiva, teeth, if any, and bony structures. The software will also permit manipulation of the displayed image to allow virtual rotation of the "patient" in any axis. Being able to rotate the virtual "patient" permits the dental professional to more effectively plan hole locations and trajectories by being able to assess bony structures from multiple angles. This will in turn result in the optimization of implant location and stability when implants are surgically placed in the patient's jaw.

For patients with a small edentulism, mapping can be done with the aid of the crowns of existing teeth. For patients who are largely or completely edentulous, mapping can be done with the aid of x-ray markers, which are visible on both the CT and optical scans.

Figure 6:
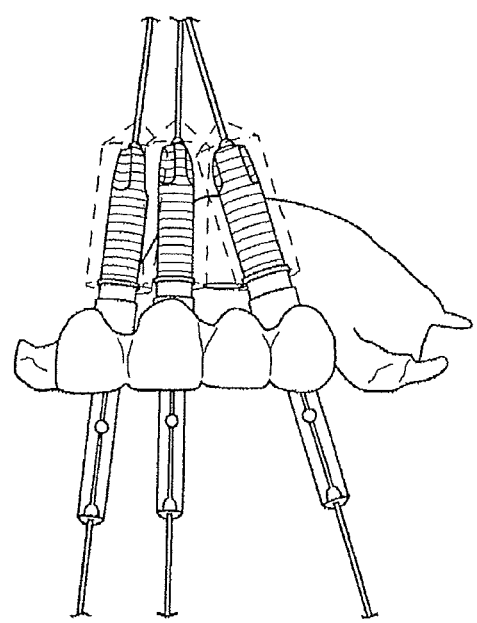
FIG. 6 is a computer display showing an example of a virtual treatment plan produced using the NobelGuide™ system.

The next step in the process involves developing the virtual treatment plan. Generally, the treatment plan will include determining the location, angle (trajectory), depth, orientation of implant head, and width, of holes to be created in the patient's jaw during the surgical phase of the process. In some embodiments, the treatment plan can be a virtual treatment plan, created using computer algorithms that permit the virtual placement of one or more "implants" in a 3-D representation of the patient's jaws and/or oral surface contours. An example of a treatment plan display is provided in FIG. 6.

In planning treatment, the dental professional is provided a number of possible virtual operation choices. For example, where a patient has a small edentulous region, the space can be virtually reconstructed by selecting an appropriately sized and shaped "tooth" from a database library. Where one or more teeth are to be extracted, the socket size can be estimated from the root shape. Thus, implants from the library can be conceptually "placed" according to the estimated existing alveolar volume and socket size following virtual extraction.

Figure 7:
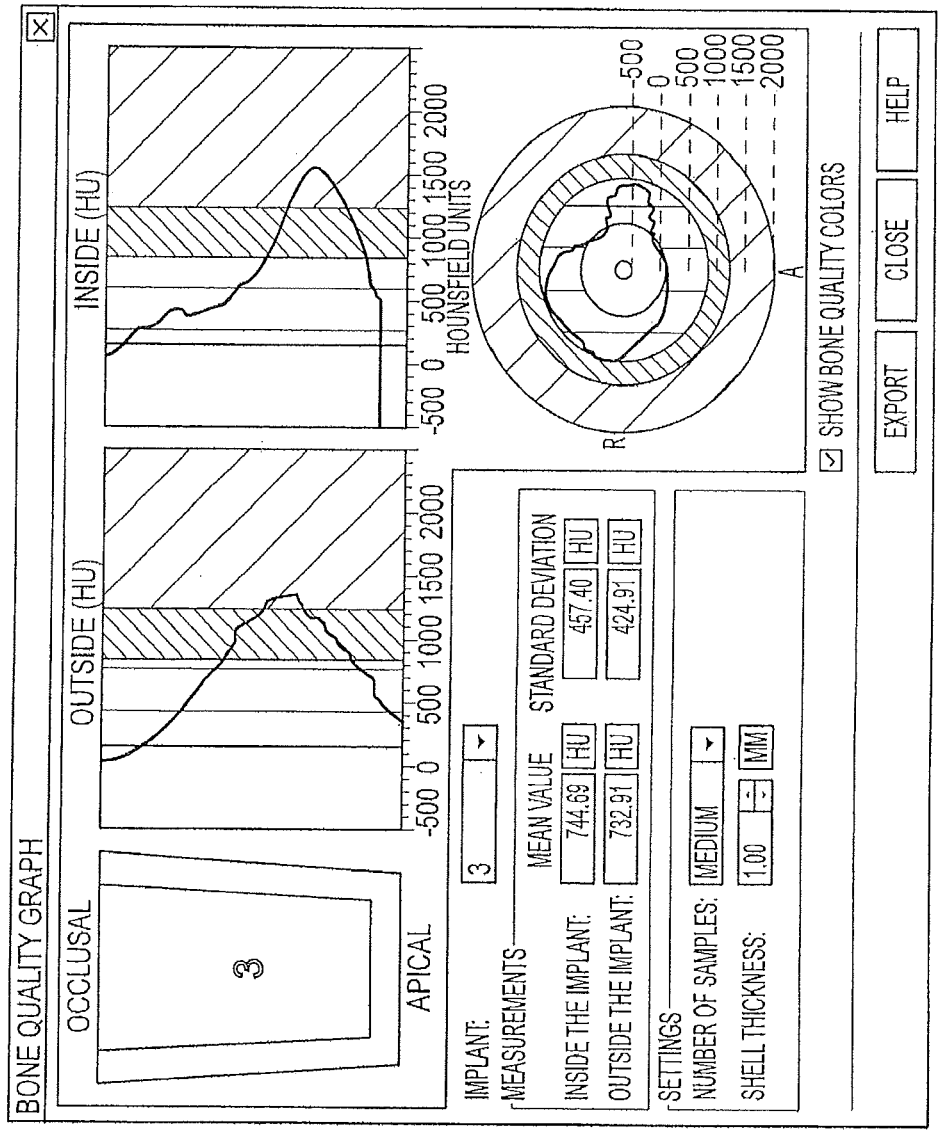
FIG. 7 is a computer display showing a bone density software tool (Simplant).

In some embodiments, the system will include an assistant module. The assistant module will generally comprise a software program that receives inputs from the CT scanner or other devices, and outputs information about bone density or other relevant structural information with relation to the intended site of implantation. The assistant module can be further programmed to automatically select a most preferential implant site, or to warn the surgeon about possible problems with nerves or other objects one would wish to avoid damaging during surgery. For example, the assistant module could provide the dental professional with an output related to bone quality that relates to bone density (e.g., Hounsfield unit map), as shown in FIG. 7. In some embodiments, a treatment planning module and an assistant module can be the same.

In some embodiments, the treatment planning module could be entirely automated, such that based on the CT scan and surface imaging data, the planning module could plan the placement of dental implants based on the same "rules" a dental professional would use in determining where best to place an implant.

In some embodiments, the treatment planning module can be used to perform a virtual extraction of a tooth, or teeth. This feature allows for simultaneous extraction, implant placement, and prosthesis delivery. None of the prior art systems provide this capability.

Machined Master Replica

It is to be understood that any and all references to the use of any machine, for example any computer-numerical controlled multi-axis milling machine (CNC), in the description that follows are merely exemplary, and are not in any way limiting to the scope of the disclosure or claims. Thus, any apparatus or device that is able to perform any steps of any method or to produce any object as described herein is intended to fall within the scope of the invention.

In some embodiments, the virtual treatment plan will be used in the production of a replica of the patient's oral structures. In some embodiments, a pre-shaped resin block can be mounted on a computer-numerical controlled multi-axis milling machine (CNC1), although any machine capable of shaping objects can be used. The block can be pre-shaped to permit reproducible placement of the resin block on the CNC1, such that a number of manipulations involving either the CNC1 or other dental laboratory procedures can be performed on the resin block while maintaining registration of the physical block with the virtual treatment plan.

After mounting the block on the CNC1, milling of the resin block can be performed to produce a milled block that replicates the patient's oral surface features. While the underlying bony or other tissue information is not milled into the block, the system nevertheless includes data corresponding to the position of underlying structures relative to the surface features, as well as data related to the treatment plan developed with the treatment planning software.

The relevant clinical data of a patient (e.g., teeth, edentulous ridges, gums, and "virtual extractions") can be reproduced on the resin block using the CNC1. Next, implant analogs (replicas of the surgical implants will be installed in the patient's jaw) can be placed into the machined resin block according to the virtual treatment plan. In some embodiments, placing of the analogs involves first drilling holes into the resin block of a diameter, depth, trajectory, and implant head orientation, based on that determined during virtual treatment planning. The placement and positioning of the analogs can be controlled by the CNC1, acting on instructions received from the treatment planning software.

Figure 8:
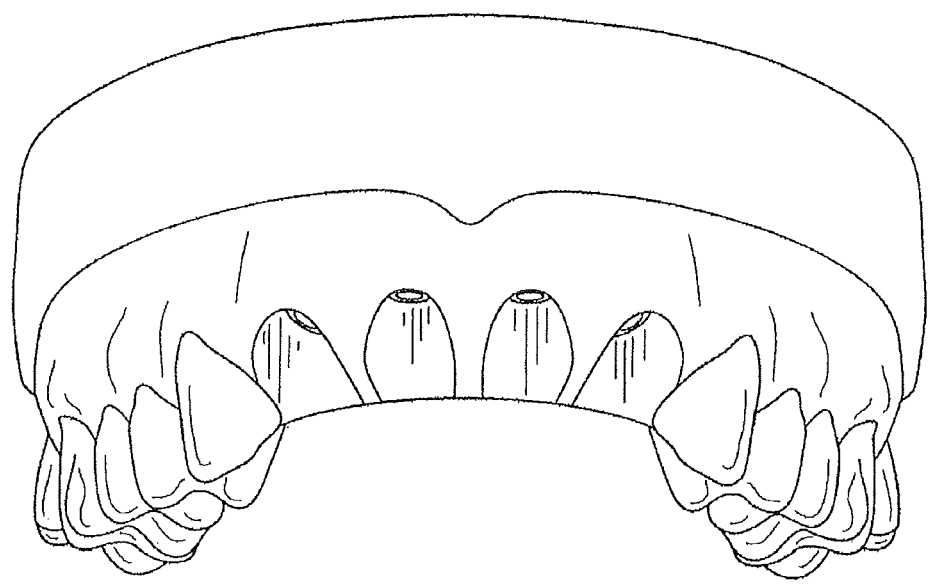
FIG. 8 is a display of a machined master model (MMR) after virtual extraction of the four incisors.

An example of a simulated replica with mounted analogs is provided in FIG. 8. The oral structures represented in FIG. 8 are made from a cast, but replicate what a machined replica with installed analogs would look like.

The result is a model of the patient's oral structures, with implants installed. This model is termed a machined master replica (MMR). The MMR can be placed in a semi-adaptable articulator along with a functional prosthesis acrylic replica to confirm proper occlusion.

The MMR provides several advantages over prior art methods of making oral replicas. The MMR can be made of a variety of materials that are stable and easy to work with. For example, the MMR can be made from a resin block immediately upon completion of the treatment planning. Unlike prior art methods of casting, no time is required to wait for the casting material to harden. In addition, the use of an MMR avoids the need to wait for the availability of the 3-D printed surgical guide, which prior art methods use in the manufacture of the prosthesis.

In addition, as the virtual treatment plan includes in its database the relationship between the surface features, and the underlying bony structures into which the implants will be installed, the dental professional can use an MMR as a practice model on which to replicate the treatment plan to confirm the esthetic and functional quality of the treatment plan, prior to delivering the prosthesis to a live patient.

In some embodiments, the MMR can be used as a template with which to fashion a prosthesis. In making the prosthesis, traditional laboratory methods can be used.

Figure 9:
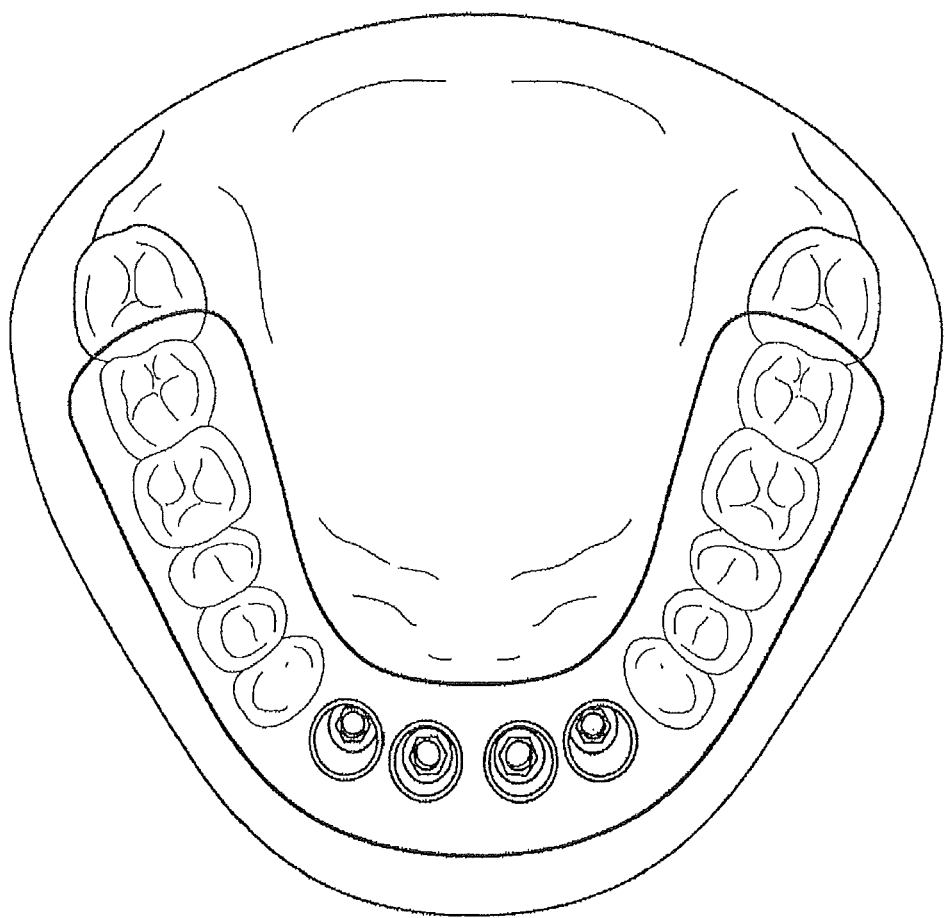
FIG. 9 is a display of the same MMR covered with a laboratory made surgical guide.

The MMR can also be used in order to fashion a surgical guide, as shown in FIG. 9. The surgical guide can be molded using the MMR as a template. Since the guide is being molded from the MMR, materials such as self-curing polymers or plastics can be used as the mold material. This will avoid problems due to the nature of materials used to make surgical guides by sterolithography. For example, in some embodiment, the surgical guide can be made from materials that are not adversely affected by moisture, or UV light, and which are chemically stable enough to permit sterilization by autoclaving, or alternatively, by chemical sterilization methods. Surgical guides can also be fashioned from metal or heat resistant plastic as well. Further, since an MMR can be rapidly made, it is possible to produce several identical MMR replicas, thus allowing different aspects of the procedure to be performed at the same time. For example, with three MMRs, one can be used to manufacture a surgical guide, one can be used for practicing the surgery, and one could be used to manufacture the prosthesis, all of which could occur essentially simultaneously. The MMR can also be used for simulating tooth extractions.

After making a surgical guide using the MMR as a template, drill guides can be placed into the surgical guides. In some embodiments, drill guides comprise generally open tubes with a lumen of a pre-selected diameter. The drill guide can be mounted into the surgical guide, as shown in FIG. 9, where they define the location and trajectory of the hole to be placed in the patient's jaw and which receives the implant. The central hole in the drill guide is sized large enough to accommodate the desired drill bit without resulting in binding of the bit in the sleeve while the drill is operating. Binding of the drill bit in the guide can cause excessive friction which in turn leads to heat generation during the drilling process. Excessive heat can damage adjacent tissues, and so the drill guide must be sized to allow free rotation of the drill bit. Drill guides can be fashioned from a number of suitable materials, including, without limitation, surgical steel, ceramics, polymers, and the like.

In some embodiments, a treatment planner can comprise a human being. In some embodiments, a human treatment planner can provide input by, e.g., marking a planned hole parameter on a virtual or physical 3-D representation at the planned location site of an endosseous implant with, for instance, a computer marking device, e.g., a mouse or a touchscreen device or a physical marking device, e.g., a pen, a pencil, or a chisel, respectively. In some embodiments, a treatment planner can comprise a computer program. In some embodiments, a computer treatment planner can provide input by, e.g., directing the marking a planned hole parameter on a virtual or physical 3-D representation at the planned location site of an endosseous implant with, for instance, a computer marking device or a physical marking device, respectively.

Calibration Template

Figure 10:
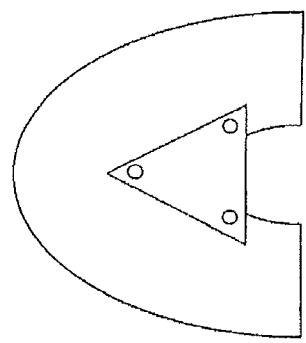
FIG. 10 is a view of an embodiment of a calibration transfer template (CTT); the left panel depicts a top view of the CTT, while the right panel depicts side sectional views of the CTT taken at different positions across the CTT, as depicted by the arrows. The bottom panel illustrates one example of an alignment of the CTT and the MMR.
Figure 10:
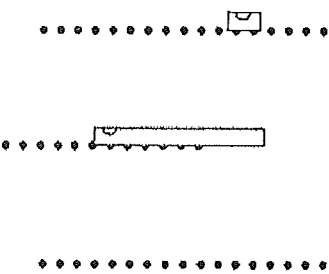
Figure 10:
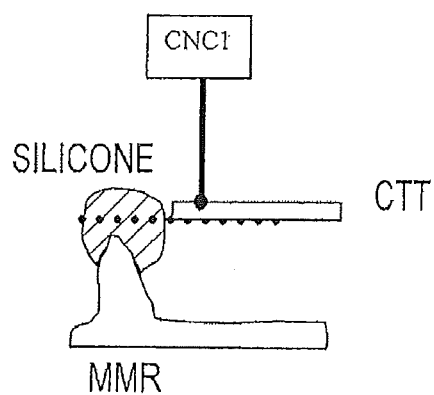

In some embodiments, a CTT is produced, as shown in FIG. 10. The CTT will generally be fashioned from a rigid material, and will include three or more calibration marks, which can be in the form of depressions placed at various locations on a surface of the CTT. In some cases the CTT is roughly triangular in shape and includes calibration marks arranged near each vertex of the CTT.

The CTT can be adapted to the MMR using silicone or other suitable adhering material. Once the CTT has been immobilized relative to the MMR, the combination of replica and calibration template is mounted on a CNC1 machine. The CNC1 machine is then used to record to relative position of the calibration marks in the CTT, and this data is included in the virtual treatment plan data. In some embodiments, recorded positional calibration data and the CTT are later used to calibrate a second CNC machine, for example, a CNC2 machine, which can be used in performing the surgery, as well as in the installation of the prosthesis.

Surgical Procedures

Figure 11:
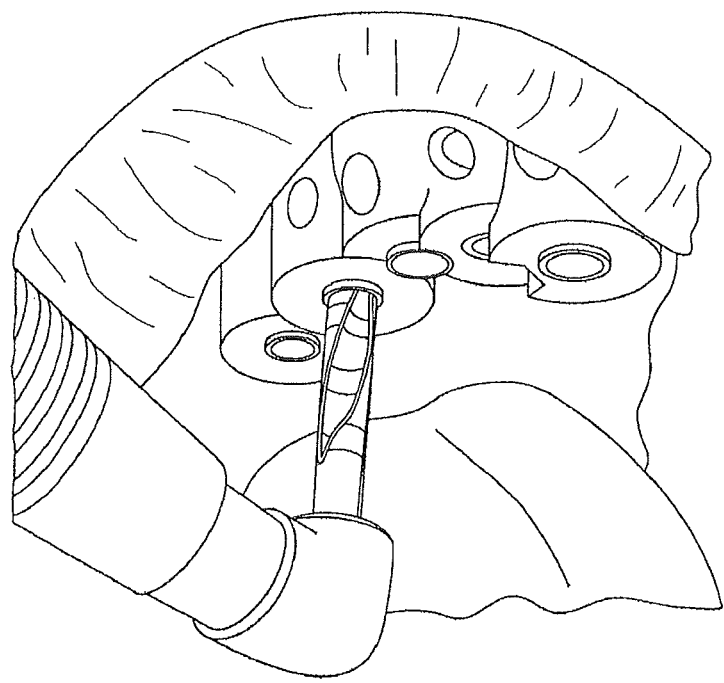
FIG. 11 is a view of a surgical guide, including drill guides, produced by the NobelGuide™ surgical system.

Prior art methods of surgical delivery of implants generally employ a common approach. A surgical guide is mounted on the patient's jaw. The surgical guide includes drill guides that direct the dental professional's hand in terms of location and trajectory of holes to be drilled into the jaw and into which implants will eventually be mounted. An example of a surgical procedure using a physical guide is shown in FIG. 11.

Figure 12:
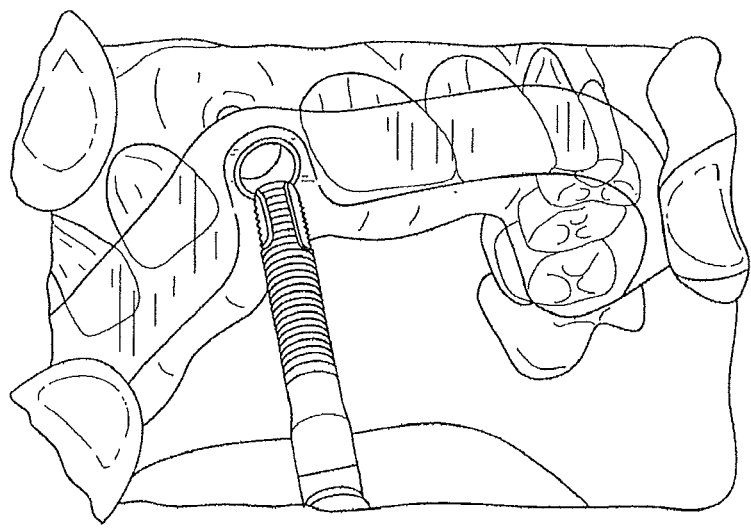
FIG. 12 is a view of an extraction with simultaneous implant placement using a surgical guide fabricated from a MMR after virtual extraction, as performed using the NobelGuide™ surgical system.

In some embodiments of the present disclosure a surgical guide, like that shown in FIG. 9, can be produced using the MMR. The surgical guide includes one or more drill guides corresponding to desired locations for performing an osteotomy according to the treatment plan. The surgical guide can be mounted in the patient's mouth by standard procedures. Unlike prior art guide produced by sterolithography, the surgical guide of the present disclosure is produced using the MMR as a template, and can be made from materials more suitable for use in an aqueous, and preferably hygienic working environment. This provides, among other things, a better fitting surgical guide, and one that can be produced nearly immediately after completion of the treatment planning phase.

Where a surgical guide device is used, the dental professional will place the device in the patient's mouth, confirm correct alignment, then fix the surgical guide in place. The dental professional then uses an appropriate sized drill bit to form the holes in the jaw into which the implants are subsequently placed. An example of a surgical guide in place, with the osteotomy complete, and the implant in position for delivery is shown in FIG. 12. In some embodiments, a guide module and a bifurcation module can be the same device.

The surgical guide is designed to ensure that the hole drilled follows the desired path and extends to the desired depth, as determined in the treatment plan. Once the holes are drilled, the dental professional can then install the implants into the holes. In some embodiments the implant is threaded, and thus is screwed into the newly formed hole. Other shapes and configurations are also useful in conjunction with the methods described herein, and so the particular style of implant is not considered to limit the disclosure in any way. The implants themselves can be made from a variety of materials that are biocompatible, and which will encourage bone growth around the implant in order to further stabilize it.

In some embodiments, for example the method outlined in FIG. 4, a surgical guide is not used, but instead surgery is performed directly by a surgical robot, programmed with information in the treatment plan. Where "guideless" surgery is performed, treatment planning, surgery, and delivery of the prosthesis can be done in a completely virtual environment. In this case, to ensure accuracy of the process, the anatomical structures of the "live" patient, and those of the "virtual" patient can be calibrated with respect to each other.

This can be done in several ways. In one example, the CTT and MMR coupled to each other, and then probed by the CNC1 machine. The CNC1 determines the relative position of calibration marks included on the CTT, and maps the position of those marks with respect to analogous calibrations on the MMR. Note that the position of underlying (i.e., non-surface) structures have already been mapped relative to the surfaces features as represented in the MMR. Thus, the calibration process provides data that relates the surface features, the underlying structures, and the treatment plan, to produce a comprehensive dataset that allows the CTT to calibrate, for example, a CNC2 machine so that it can accurately replicate the treatment plan on the live patient.

In some embodiments, the calibration marks can be hemispherical depressions in the CTT that match the shape of a probe end on an arm of the CNC1 machine, as illustrated in FIG. 10. The precise shape, size and location of calibration marks on the CTT are not limiting, nor is the precise structure of the probe mechanism on the CNC1 machine.

The CNC2 machine can be configured to move a drill bit along a trajectory with respect to the patient's oral structures, and to drill holes in the patient's jaw to a predetermined depth, based on the virtual treatment plan. Using a CNC2 surgical robot permits automated surgery without the need for a surgical guide device. In this way, any error in positioning a surgical guide in the patient's mouth can be avoided and thus the procedure can nearly perfectly reproduce the treatment plan on the patient. It will be understood that the use of a CNC2 machine as a surgical robot is merely an example, and is not limiting to the scope of the disclosure. Any surgical robot, or like device, that can perform any step or produce any product as described herein, is considered to be included within the scope of the present disclosure. Thus, in some embodiments, a single machine suitably equipped, is able to perform all the tasks as described herein. Accordingly, the use of separate CNC1 and CNC2 machine is merely exemplary and does not limit the disclosure in any way.

In performing surgery using a surgical robot it sometimes useful to provide the surgical robot, for example a CNC2 machine, with an accurate 3-D frame of reference with respect to the patient's oral structures. As discussed, one aspect of this involves the accurate calibration of the CTT with respect to the MMR and the treatment plan. In addition, the patient's head must be secured relative to the CNC2 surgical robot, such that the frames of reference between the CTT, the patient, and a CNC2 machine are maintained in registration throughout the surgery.

Figure 13:
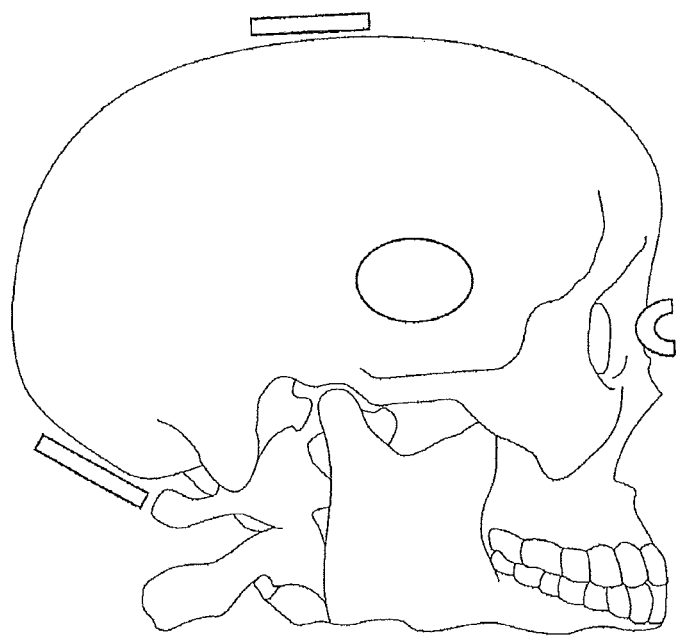
FIG. 13 is a radiographic side view of a patient's skull and/oral structures, and one example of extra-cranial support placements (open white shapes overlying the radiograph) when performing surgery on the upper jaw.
Figure 14:
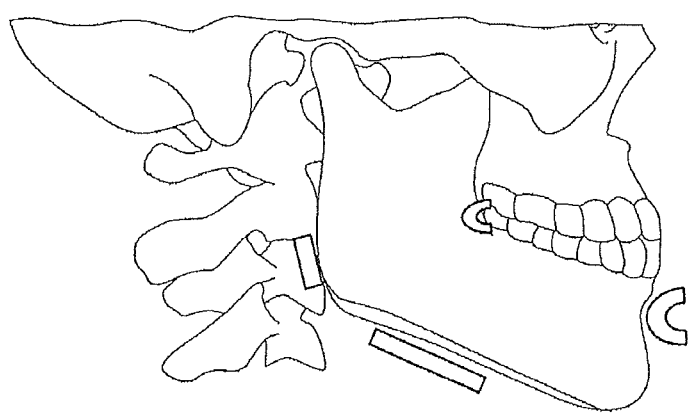
FIG. 14 is a radiographic side view of a patient's skull and/oral structures, and one example of extra-cranial support placements (open white shapes overlying the radiograph) when performing surgery on the lower jaw.

In some embodiments, stable, externally located cranial supports are used to immobilize a CNC2 machine relative to the patient's skull and/or oral structures. As shown, supports can be used to immobilize either the upper jaw or the lower jaw. In some cases both upper jaw and lower can be immobilized.

Where surgery is to be performed on the upper jaw, it is sufficient to use a number of extra-oral supports, as the upper jaw is anatomically fixed relative to the skull, as illustrated in FIG. 13. When performing lower jaw surgery, it can be advantageous to use both extra-oral supports as well as intra-oral supports, as shown in FIG. 14.

Figure 15:
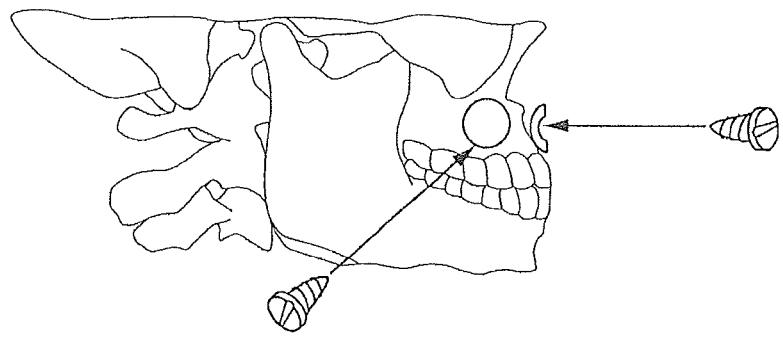
FIG. 15 is a radiographic side view of a patient's skull and/oral structures, and an example of an intra-oral support fixated with orthopedic screws, one facial and two lateral, for use when performing surgery on the upper jaw.
Figure 16:
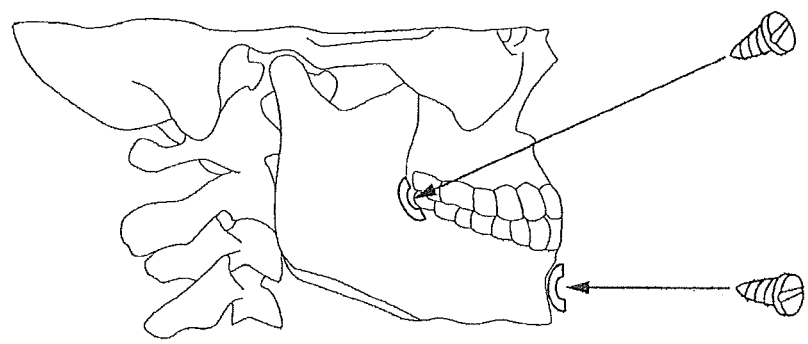
FIG. 16 is a radiographic side view of a patient's skull and/oral structures, and an example of an intra-oral support fixated with orthopedic screws, one on the symphysis and two on oblique branches of the mandible, for use when performing surgery on the lower jaw.

The extra-cranial support system is effective to couple the 3-D frames of reference of the CNC2 surgical robot, the CTT, the treatment plan, and the patient. The connection can be released if desired, for example, if the need arises to abort the surgical procedure for safety or other reasons.

Where this external support system is not sufficiently stable, for example, due to unusual anatomical features of the patient, a modified support system can be used. In one example, the support can be fixed intra-orally by three small arms fixated to the jaw through the mucosa using orthopedic fixation screws, for example 1.5 to 3 mm diameter and 5 to 10 mm long screws, as illustrated in FIGS. 15 and 16.

Once the patient has been immobilized relative to the surgical robot, for example, a CNC2 machine, the 3-D frames of references can be aligned, such that the CNC2 machine is in registration with the location of the patient's surface features, the underlying bony structures, and the treatment plan. In one example of a method for aligning the patient and the surgical robot, the CTT is placed in the patient's mouth, and a robotic arm of the CNC2 can be used to map the location of the calibration marks on the CTT. As these calibration marks were previously mapped and recorded relative to the MMR, once the calibration of the CNC2 is complete, the CNC2 will possess an accurate relative map of the orientation of the patient's oral structures, as represented by the MMR, as well as the location of underlying structures present in the virtual patient representation (VPR), as well as the data corresponding to the treatment plan.

Calibration can include additional checks to ensure the fidelity of the alignment between the VPR and the patient's actual oral structures. In some embodiments, a check procedure can include directing the CNC2 probe to touch various pre-determined locations within the patient's mouth. In patients with teeth, these could be specific spots on an existing tooth. Here the surgeon could easily confirm that the CNC2 was able to precisely locate specific positions, thus confirming the fidelity of the calibration procedure. In edentulous patients, other markers could be used. For example, small minimally invasive marker devices could be planted at various points along the gums, and the CNC2 could be directed to touch those points to confirm the calibration is accurate.

Once the CNC2 has been calibrated, the osteotomy can take place. Various procedures are available, including both "flap" and "flapless" surgery. When flap surgery is used, a portion of the overlying gum tissue is dissected and peeled back to give the dental professional direct access and a view of the underlying bone. When flapless surgery is used, the dental professional can, optionally, use a round tissue punch to remove soft tissue overlying the bone at the intended implant site, exposing the bone beneath. In some methods, the dental professional can drill directly through the mucosa.

Once access to the underlying bone is achieved, a surgeon can drill a hole for an implant. Holes can be drilled by the surgeon using a surgical guide made as described above. In some cases, the drilling of holes will be performed by the CNC2 surgical robot. Using the CNC2 machine obviates the need for a surgical guide device as all of the treatment plan parameters are programmed into the software that directs the CNC2 machine. Therefore, the CNC2 machine will be directed to drill holes in the patient's jaw at a pre-determined trajectory, and to a pre-determined depth. The caliber of the hole will be dictated by the drill bit used.

In some embodiments, the operator will manually change the drill bit mounted on the CNC2 drill head according to the treatment plan. In some embodiments the tool selection can also be made to be automatic, such that the CNC2 machine includes additional capabilities to change tools according to software directions included in the treatment plan data.

The CNC2 machine can include, without limitation, other features useful in the surgical procedure, such as apparatus for cleaning out the freshly drilled holes and for removing debris, blood, or saliva, or camera systems to enable remote viewing or recording of the procedure. The CNC2 can also include display capabilities that output various parameters such that the surgeon can monitor progress of the treatment plan. The CNC2 can also include an emergency interrupt system so that in case of emergency the surgery can be safely and quickly paused or terminated. The surgical robot can operate regardless of the orientation of the patient's head.

Installing the Prosthesis

Once the implant holes are completed and cleaned, the CNC2 machine can also be used to deliver the prosthesis. As the CNC2 includes in its programming the entire treatment plan, including the shape and intended placement of the prosthesis, it can be readily adapted to put the prosthesis in place, as well as complete any other functions associated with the installation. Installation of the prosthesis by the CNC2 surgical robot can include, without limitation, placing the prosthesis on the implant abutments and then fastening the prosthesis to the implant(s). In some embodiments a biostable adhesive is used to affix the prosthesis to the implant. In some embodiments, the prosthesis can be affixed by fasteners such as screws and the like. In some embodiments a prosthesis can additionally be anchored to pre-existing teeth.

Flow Chart

Figure 17:
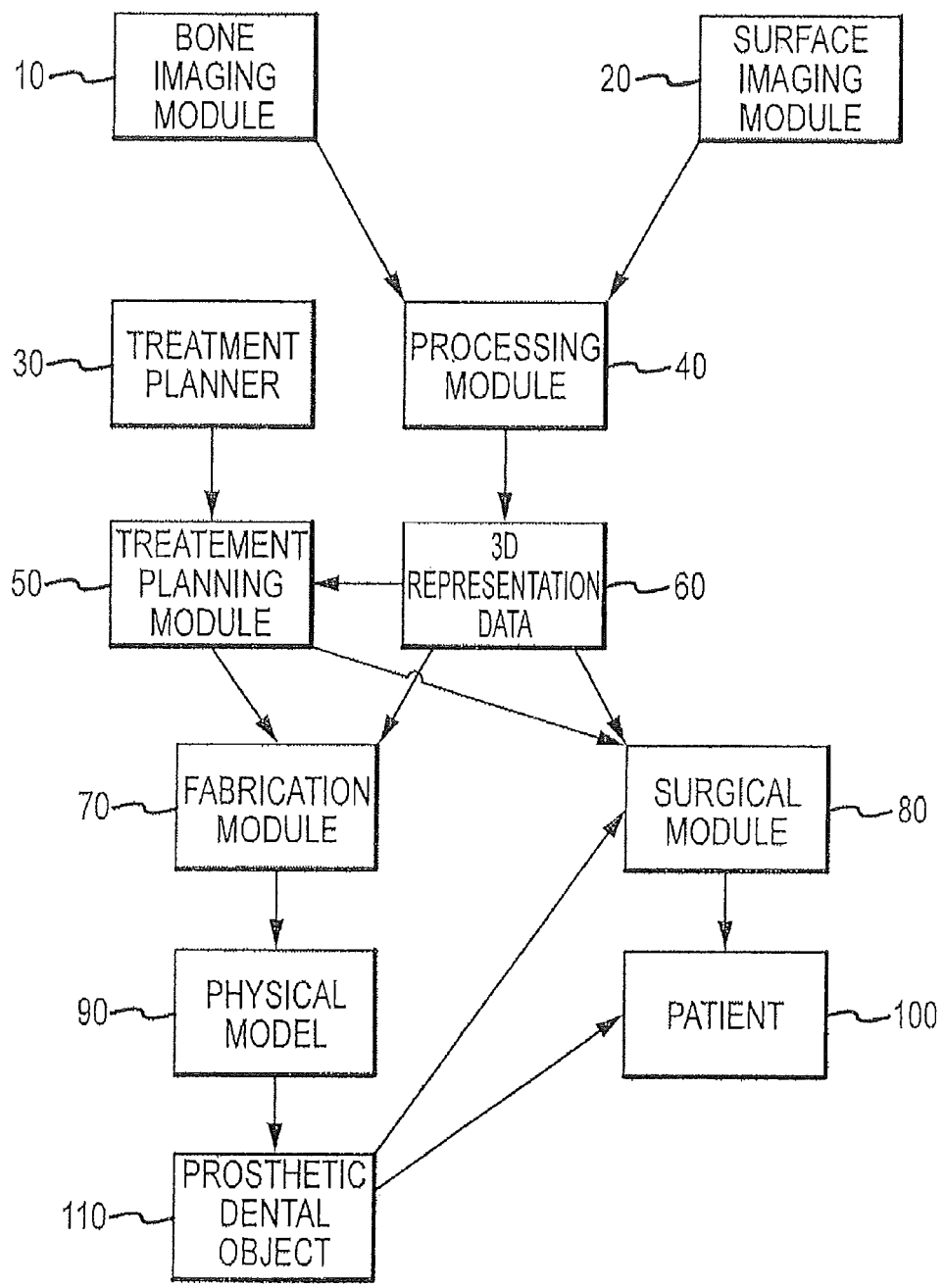
FIG. 17 illustrates certain embodiments of systems and methods of the present invention, in the form of a flow chart of exemplary modules and exemplary flows of inputs and outputs for and between them.

As illustrated in FIG. 17, certain systems of the present invention provide for planning an oral or facial endosseous implantation in a patient, and comprise a processing module 40; a bone imaging module 10 that communicates bone data to the processing module 40, the bone data representative of at least a portion of a bone of the skull of the patient; a surface imaging module 20 that communicates surface data to the processing module 40, the surface data representative of at least a portion of a surface, of the patient, that is apart from the bone. In certain embodiments, a single module can comprise both the bone imaging module and the surface imaging module. In certain embodiments, the processing module 40 processes bone data and surface data into an output comprising three-dimensional (3-D) representation data 60 indicative of at least one of an oral structure and a facial structure of the patient.

In certain embodiments, a fabrication module 70, produces, based on the 3-D representation data 60 and/or inputs from a treatment planning module 90, a physical model 90 of the at least one of the patient's oral structure or facial structure, the model indicating a planned location of an endosseous implant. In some embodiments, a treatment planning module 50 outputs, based on a combination of the 3-D representation data 60 and input received from a treatment planner, information, e.g., a treatment plan, to a machine-readable medium, the treatment plan comprising a parameter for a planned hole in the portion of the bone; wherein the planned hole is configured to receive the endosseous implant. In some embodiments, the parameter comprises at least one of a spatial location, a depth, a diameter, and an angular orientation of the planned hole. In some embodiments, a surgical module 80 guides, based on the 3-D representation data, implantation of an endosseous implant in the patient.

In some embodiments, the treatment planning module 50 outputs, based on a combination of the 3-D representation data 60 and data input received from a treatment planner 30, a treatment plan comprising a parameter for a planned hole in the portion of the bone, the planned hole configured to receive the endosseous implant. In some embodiments, such a parameter can comprise at least one of a spatial location, a depth, a diameter, and an angular orientation of the planned hole. In some embodiments, the treatment planner 30 can comprise a human being and/or a computer program. In some embodiments, the treatment planning module 50 can, in response to input from the treatment planner 30 and/or the 3-D representation data 60, output information, e.g., a treatment plan, to a fabrication module 70 or to surgical module 80. In certain embodiments, the fabrication module 70, based on the information from the treatment planning module 50 and/or the 3-D representation data 60, produces the physical model 90. In certain embodiments, a prosthetic dental object 110, e.g., an implant, a prosthetic tooth, or a combination thereof, can be formed, at least in part, based on the physical model 90. In certain embodiments, the surgical module, based on outputs from the treatment planning module 50 and/or the 3-D representation data 60, implants, or direct the implantation of, the prosthetic dental object 110 in the patient 100.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A system, for planning and performing a surgical procedure, the system comprising:
    a processing portion for processing the hard tissue of a patient that communicates hard tissue data to the system, including bone density, contours of oral structures and upper and lower dentition, wherein hard tissue data is communicated to the system in the form of a three-dimensional (3-D) representation of the hard tissue;
    a treatment planning module that (i) merges data received from the processing portion and the hard tissue data for desired treatment of the patient, wherein an image for display including a 3-D representation of both surface features and bone structures of the patient is generated based on the merged data, the image being manipulable to allow virtual rotation of the image in any axis to allow for effective planning of hole locations and trajectories of the oral structures, and (ii) generates a virtual treatment plan permitting the placement of one or more implants into the 3-D representation of both the surface features and the bone structures of the patient; and
    a surgical robot apparatus to perform at least part of the surgical procedure based on at least the virtual treatment plan.

2. The system of claim 1, wherein the surgical procedure is a surgical technique on the patient's hard tissue.

3. The system of claim 1, further comprising a surgical module that based on the 3-D representation of both surface features and bone structures guides the medical professional in the surgical procedure.

4. The system of claim 1, wherein the surgical robotic apparatus is an active robotic apparatus whereby the surgical robotic apparatus is controlled by a computer program.

5. The system of claim 1, wherein the surgical robotic apparatus is a passive robotic apparatus whereby the surgical robotic apparatus is controllable by a medical professional with limited feedback from the surgical robotic apparatus.

6. The system of claim 1, wherein the treatment planning module generates the virtual treatment plan by combining the 3-D representation of both the surface features and the bone structures and input received from a treatment planner.

7. The system of claim 1, wherein the system may digitally fabricate a computerized image of the patient's hard tissue to illustrate the treatment plan for the individual patient.

8. The system of claim 1, further comprising:
    a surgical guide based on the 3-D representation of both the surface features and the bone structures, the surgical guide utilized by the robotic surgical apparatus.

9. A method for planning and performing a surgical procedure, the method comprising:
    providing a system for planning and performing the surgical procedure including:
        providing a processing portion for processing hard tissue information about a patient including bone density, contours of oral structures and upper and lower dentition;
        communicating hard tissue data in the form of a three-dimensional (3-D) representation;
        merging data received from the processing portion and the hard tissue data for desired treatment of the patient, wherein an image for display including a 3-D representation of both surface features and bone structures of the patient is generated based on the merged data, the image being manipulable to allow virtual rotation of the image; in any axis to allow for effective planning of hole locations and trajectories of the oral structures
        generating a virtual treatment plan permitting the placement of one or more implants into the 3-D representation of both the surface features and the bone structures of the patient; and
        providing a surgical robot apparatus configured to receive the virtual treatment plan, wherein
        the surgical robot apparatus is configured to perform at least part of the surgical procedure based on at least the virtual treatment plan.

10. The method of claim 9, wherein the surgical procedure is a surgical technique on the patient's hard tissue.

11. The method of claim 9, wherein the surgical robot apparatus guides a medical professional in the surgical procedure.

12. The method of claim 9, wherein the surgical robotic apparatus is an active robotic apparatus whereby the surgical robotic apparatus is controlled by a computer program.

13. The method of claim 9, wherein the surgical robotic apparatus is a passive robotic apparatus whereby the surgical robotic apparatus is controlled by a medical professional with limited feedback from the surgical robotic apparatus.

14. The method of claim 9, wherein a treatment planning module combines the 3-D representation of both the surface features and the bone structures and input received from a treatment planner and outputs the treatment plan for implementation of the treatment plan by the surgical robot apparatus.

15. The method of claim 9, further comprising the step of: digitally fabricating a computerized image of the patient's hard tissue to illustrate the treatment plan for the individual patient.

16. The method of claim 9, further comprising the steps of:

digitally fabricating a computerized image which is utilized by the surgical robotic apparatus.

17. A method for planning and performing a surgical procedure, the method comprising the steps of:

processing hard tissue of a patient including bone density, contours of oral structures and upper and lower dentition;

merging data representing surface contours of the patient's oral structures and underlying bony structures and the hard tissue data, wherein an image for display including a 3-D representation of both surface features and bone structures of the patient is generated based on the merged data;

communicating 3-D representation of both surface features and bone structures and allowing manipulation of the image to allow virtual rotation of the 3-D representation of both surface features and bone structures in any axis to allow for effective planning of hole locations and trajectories of the oral structures; and performing at least part of the surgical procedure with a surgical robot apparatus based on at least the 3-D representation of both surface features and bone structures.

18. The method of claim 17, wherein the surgical robot apparatus is guided by a medical professional in the surgical procedure.

19. The method of claim 17, wherein the surgical robotic apparatus is controlled by a computer program.

20. The method of claim 17, wherein the surgical robotic apparatus is controlled by a medical professional with limited feedback from the surgical robotic apparatus.

* * * * *